US012805933B2

(12) United States Patent
Vincelette

(10) Patent No.: US 12,805,933 B2
(45) Date of Patent: Nov. 24, 2026

(54) NANODIAMOND TEMPERATURE THERMOMETER FOR STATIC MONITORING OF TISSUE TEMPERATURE DURING MRI-GUIDED LASER ABLATION

(71) Applicant: MEDTRONIC NAVIGATION, INC., Louisville, CO (US)

(72) Inventor: Rebecca L. Vincelette, Arvada, CO (US)

(73) Assignee: MEDTRONIC NAVIGATION, INC., Louisville, CO (US)

(*) Notice: Subject to any disclaimer, the term of this patent is extended or adjusted under 35 U.S.C. 154(b) by 842 days.

(21) Appl. No.: 18/042,499

(22) PCT Filed: Oct. 12, 2021

(86) PCT No.: PCT/US2021/054564
§ 371 (c)(1),
(2) Date: Feb. 22, 2023

(87) PCT Pub. No.: WO2022/081565
PCT Pub. Date: Apr. 21, 2022

(65) Prior Publication Data
US 2023/0320785 A1 Oct. 12, 2023

Related U.S. Application Data

(60) Provisional application No. 63/091,678, filed on Oct. 14, 2020.

(51) Int. Cl.
*A61B 18/22* (2006.01)
*A61B 18/24* (2006.01)
*A61B 90/00* (2016.01)
*A61B 18/00* (2006.01)

(52) U.S. Cl.
CPC .............. *A61B 18/22* (2013.01); *A61B 18/24* (2013.01); *A61B 90/37* (2016.02);
(Continued)

(58) Field of Classification Search
CPC . A61B 18/22; A61B 2018/2211; A61B 90/37; A61B 18/24; A61B 2090/374;
(Continued)

(56) References Cited

U.S. PATENT DOCUMENTS 8,954,161 B2 * 2/2015 McCarthy ............ A61B 5/6852 607/102
2007/0179488 A1 * 8/2007 Trusty .................... A61B 18/22 606/16

(Continued)

OTHER PUBLICATIONS

International Search Report prepared by the Korean Intellectual Property Office on Feb. 3, 2022, for International Application No. PCT/US2021/054564, 4 pgs.

(Continued)

*Primary Examiner* — Aaron F Roane
(74) *Attorney, Agent, or Firm* — Sheridan Ross PC

(57) ABSTRACT

Devices, systems, and methods to measure a baseline temperature of a tissue prior to a laser ablation procedure are disclosed. The devices can be a thermometer including an optical fiber probe and a catheter. The catheter includes nanodiamonds embedded into a wall of the catheter. The nanodiamonds are excited by light from the optical fiber probe to emit a temperature dependent fluorescent light that is received by the optical fiber probe and transmitted to a temperature sensor. The temperature sensor can process the fluorescent light to calculate a temperature. The thermometer can be positioned adjacent to or within a target tissue structure prior to a laser ablation procedure to measure the baseline temperature. The baseline temperature can be input into a magnetic resonance imaging system to calculate a thermal damage estimate.

51 Claims, 5 Drawing Sheets

(52) U.S. Cl.
CPC ............... *A61B 2018/00577* (2013.01); *A61B 2018/00809* (2013.01); *A61B 2018/2261* (2013.01); *A61B 2090/374* (2016.02)

(58) Field of Classification Search
CPC ........... A61B 2018/00577; A61B 2018/00636; A61B 2018/00714; A61B 2018/00809; A61B 2018/2261; A61B 2018/2255
USPC ...................................................... 606/13–16
See application file for complete search history.

(56) References Cited

U.S. PATENT DOCUMENTS

| | | | | |
|---|---|---|---|---|
| 2016/0018269 | A1* | 1/2016 | Maurer | G01K 11/20<br>374/121 |
| 2019/0053849 | A1 | 2/2019 | Ransbury et al. | |
| 2019/0082969 | A1 | 3/2019 | Flaherty et al. | |
| 2020/0013991 | A1 | 1/2020 | Wang | |
| 2022/0273366 | A1* | 9/2022 | Varol | A61B 18/22 |

OTHER PUBLICATIONS

Written Opinion prepared by the Korean Intellectual Property Office on Feb. 3, 2022, for International Application No. PCT/US2021/054564, 4 pgs.

Laraoui et al. "Imaging thermal conductivity with nanoscale resolution using a scanning spin probe," Nature Communications, 2015, vol. 6, article 8954, 8pages.

* cited by examiner

NANODIAMOND TEMPERATURE THERMOMETER FOR STATIC MONITORING OF TISSUE TEMPERATURE DURING MRI-GUIDED LASER ABLATION

CROSS REFERENCE TO RELATED APPLICATIONS

This application is a national stage application under 35 U.S.C. 371 and claims the benefit of PCT Application No. PCT/US2021/054564 having an international filing date of 12 Oct. 2021, which designated the United States, which PCT application claimed the benefit of U.S. Provisional Patent Application No. 63/091,678 filed on 14 Oct. 2020, and titled, "Nanodiamond Temperature Thermometer for Static Monitoring of Tissue Temperature During MRI-Guided Laser Ablation," the entire disclosures of each of which are incorporated herein by reference.

TECHNICAL FIELD

The present disclosure relates generally to devices, systems, and methods used to treat a patient's tissue. More specifically, the present disclosure relates to devices, systems, and methods used to measure tissue temperature prior to and during a laser ablation procedure.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
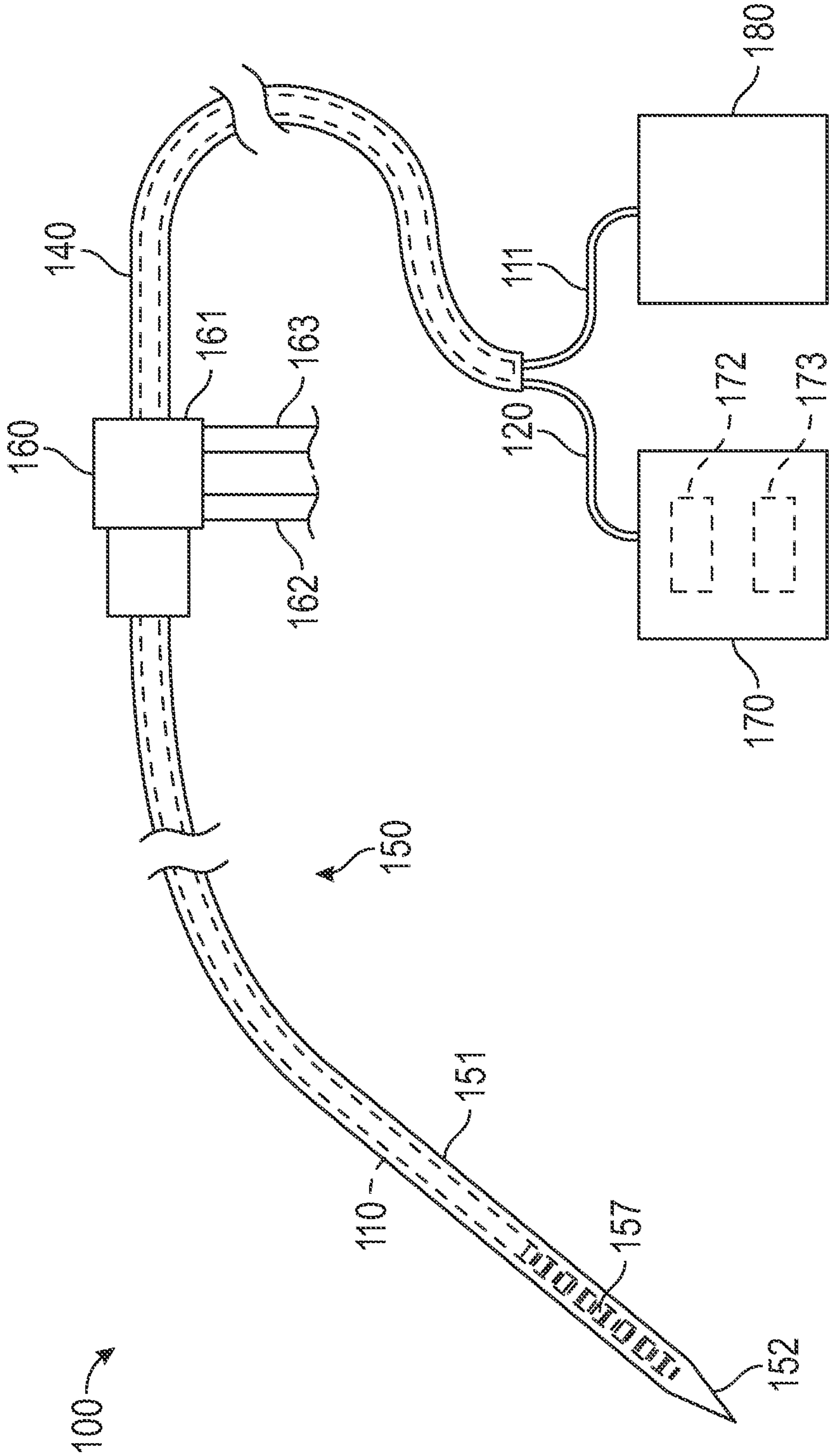
FIG. 1 is a schematic view of an embodiment of a laser ablation system including a nanodiamond thermometer.

Laser ablation, such as Laser Interstitial Thermal Therapy (LITT), is a technique for treating various tumors in the liver, the brain, the abdomen, and/or other regions of the body, as well as for treating benign lesions, such as prostate adenomas. In some therapies, a laser probe is inserted into a desired region (e.g., tumor) of treatment to deliver laser energy. After positioning the laser probe, laser energy may be emitted interstitially to irradiate target tissue and generate heat that leads to thermal tissue necrosis. Thus, LITT may be used to ablate a tumor via thermal energy generated from the laser energy while limiting side effects or additional damage to surrounding structures.

In certain instances, LITT utilizes magnetic resonance imaging (MRI) to determine a margin of the tumor to be ablated and a baseline temperature to calculate a thermal damage estimate (TDE). However, in some instances a default baseline temperature may be used to calculate the TDE for a laser ablation procedure. Use of the default base line temperature can result in overestimation or underestimation of the TDE, thus potentially resulting in ablation of non-diseased tissue surrounding the tumor and/or insufficient ablation of diseased tissue of the tumor. The ablation of non-diseased tissue may cause undesired patient morbidities, such as compromising of neural functions, seizures, excessive neural edema, etc. Insufficient ablation of the diseased tissue may cause other undesired patient morbidities, such as return of the tumor, metastasis of the tumor, death, etc.

Embodiments herein describe systems, methods, and apparatuses to assist measuring a baseline temperature of a tissue adjacent to or within a target tissue structure prior to a laser ablation procedure. The target tissue structure may include tissue that is to be ablated or tissue that is to be avoided and prevented from being ablated during an ablation procedure. While many of the examples herein describes the embodiments where the target tissue structure is a tumor to be ablated, the embodiments may be employed to protect target tissue structures that are not to be ablated.

In some embodiments, a temperature monitoring system can be used to measure a baseline temperature of tissue adjacent or within the tumor prior to or during a laser ablation procedure. The temperature monitoring system can include a temperature probe that is disposed within a catheter comprising carbon nano-crystallite nanodiamonds (e.g., fluorescent nanodiamonds) and disposed within or adjacent the tumor. The nanodiamonds are inert and biologically compatible. Nanodiamonds may be extremely small. For example, the average size of the nanodiamonds used may be 150.5±23.3 nm. In some embodiments, the temperature probe comprises an optical fiber and a laser fiber. The optical fiber may be configured to emit light to excite a nitrogen-vacancy color center of the nanodiamonds to emit an optical signal. For example, fluorescent light or a Stokes (anti-Stokes) photoluminescence may be optical signals emitted by the nanodiamonds when excited with a laser. The optical fiber may be configured to receive and/or transmit the emitted optical signal. The optical signal may be received by and processed by a temperature sensor to calculate a baseline temperature.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from a practitioner during use. The proximal end refers to the opposite end or the end nearest the practitioner during use.

FIGS. 1-4 illustrate different views of temperature monitoring systems and related components according to some embodiments. FIG. 1 is a schematic view of an embodiment of a laser ablation system including a nanodiamond thermometer. FIG. 2A is a longitudinal side view of a distal portion of a laser ablation probe of the laser ablation system of FIG. 1 including a catheter embedded with nanodiamonds. FIG. 2B is a transverse cross-sectional view at section 2B-2B of the laser ablation probe of FIG. 2A including a laser fiber and an optical fiber. FIG. 3A is a schematic view of the laser ablation system of FIG. 1 with the nanodiamond thermometer positioned in a tissue prior to a laser ablation procedure. FIG. 3B is a schematic view of the laser ablation system of FIG. 1 with the nanodiamond thermometer positioned in a tumor during a laser ablation procedure. FIG. 4A is an illustration of a thermal damage estimate using a default baseline temperature of 37 degrees C. FIG. 4B is an illustration of a thermal damage estimate using a measured baseline temperature of 35 degrees C. FIG. 4C is an illustration of a thermal damage estimate using a measured baseline temperature of 39 degrees C. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

As depicted in FIG. 1, a temperature monitoring system 100 in the illustrated embodiment comprises a temperature probe or thermometer 110, a catheter assembly 150, a temperature monitoring unit 170, and a laser source unit 180. The temperature probe 110 is disposed within the catheter assembly 150 and within a sleeve 140 disposed between the catheter assembly 150 and a proximal end of the temperature probe 110. In the depicted embodiment, the temperature probe 110 includes a laser fiber 111 coupled to the laser source unit 180 and an optical fiber 120 coupled to the temperature monitoring unit 170. In another embodiment, the temperature probe 110 includes the optical fiber 120 but does not include the laser fiber 111. The catheter assembly 150 includes a tubular body 151 coupled to a connector 160 and including a plurality of nanodiamonds 157.

Figure 2A:
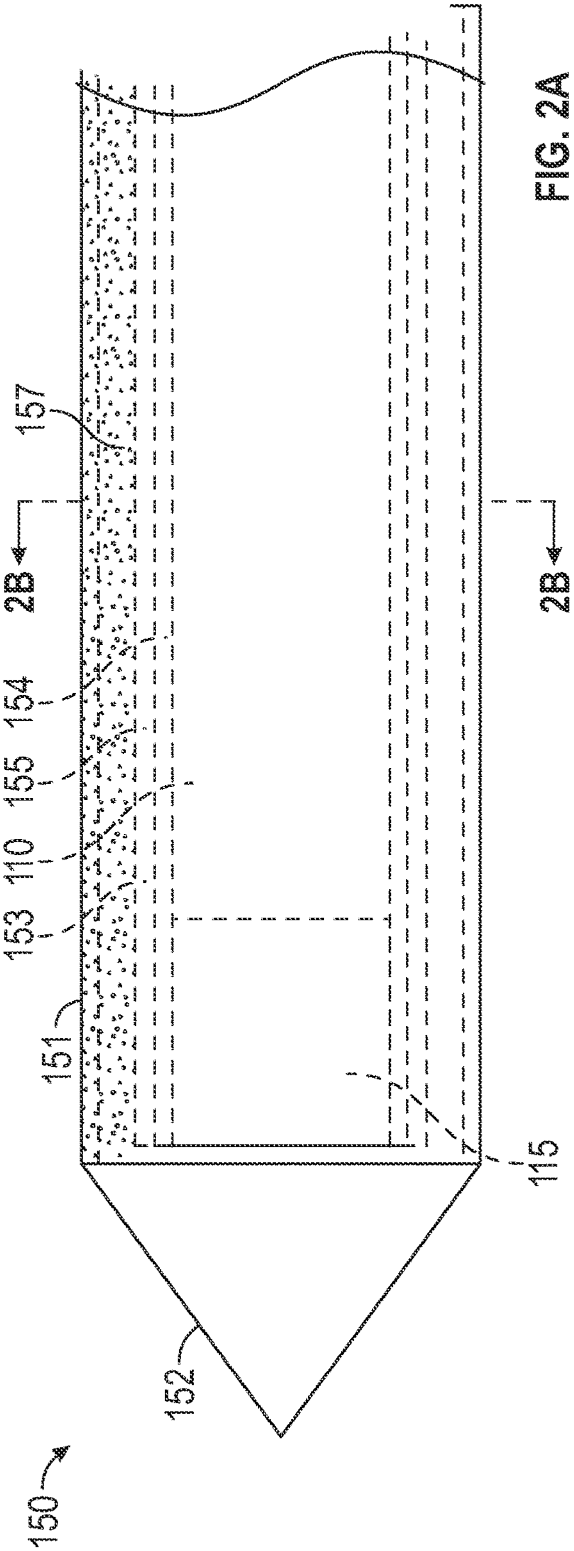
FIG. 2A is a longitudinal side view of a distal portion of a laser ablation probe of the laser ablation system of FIG. 1 including a catheter embedded with nanodiamonds.
Figure 2B:
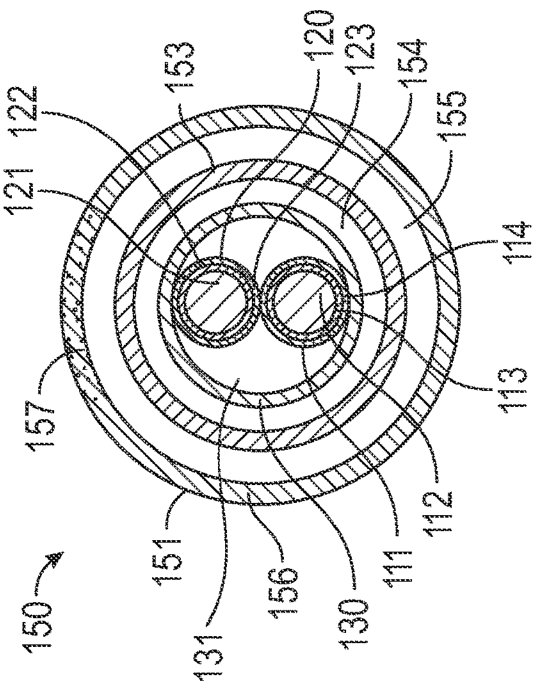
FIG. 2B is a transverse cross-sectional view at section 2B-2B of the laser ablation probe of FIG. 2A including a laser fiber and an optical fiber.

FIGS. 2A and 2B illustrate a distal portion of the catheter assembly 150 and the temperature probe 110 from side and cross-sectional views. As shown, the temperature probe 110 may include a tubular body 130 having a lumen 131 extending therethrough. A diameter of the tubular body 130 can range from about 0.1 mm to about 3 mm. The tubular body 130 may be formed of any suitable material, such as polyurethane, polyvinyl chloride, polyimide, etc. In the illustrated embodiment, the laser fiber 111 and the optical fiber 120 are disposed within the lumen 131 adjacent and substantially parallel to one another. Other relative placements of these elements are likewise within the scope of this disclosure. For example, in some embodiments, the laser fiber 111 and the optical fiber 120 may be separate probes configured to be inserted into the catheter assembly 150 individually at different times during an interstitial laser ablation procedure.

In the illustrated embodiment of FIG. 2B, the optical fiber 120 includes a core 123 having a high refractive index, a cladding 121 surrounding the core 123 having a lower refractive index, and a protective jacket 122 surrounding the cladding 121. The core 123 and the cladding 121 can be formed from any suitable material, such as glass including pure silica glass, fluoride glass, phosphate glass, or chalcogenide glass; plastics, such as acrylic or polystyrene; or a combination of both. The protective jacket 122 can be formed from any suitable material, such as polyurethane, polyvinyl chloride, polyimide, etc. The core 123 may have a diameter ranging from about 10 microns to about 600 microns. A thickness of the cladding 121 can range from about 125 microns to about 630 microns. A thickness of the protective jacket 122 may range from about 250 microns to about 1,040 microns. A proximal end of the optical fiber 120 is in communication with a light source 173 of the temperature monitoring unit 170, such that irradiated light is transmitted from the proximal end to a distal end. The proximal end of the optical fiber 120 is also in communication with a temperature sensor 172 of the temperature monitoring unit 170, such that light emitted by the nanodiamonds 157 is received and processed by the temperature sensor 172, as will be discussed below. The optical fiber 120 can be configured to transmit light from a distal end to a proximal end.

The laser fiber 111 may be disposed within the lumen 131 adjacent the optical fiber 120. In the illustrated embodiment, the laser fiber 111 includes a core 112 having a high refractive index, a cladding 113 surrounding the core 112 having a lower refractive index, and a protective jacket 114 surrounding the cladding 113. The core 112 and the cladding 113 can be formed from any suitable material, such as glass including pure silica glass, fluoride glass, phosphate glass, or chalcogenide glass; plastics, such as acrylic or polystyrene; or a combination of both. The protective jacket 114 can be formed from any suitable material, such as polyurethane, polyvinyl chloride, polyimide, etc. The core 112 may have a diameter ranging from about 10 microns to about 600 microns. A thickness of the cladding 112 can range from about 125 microns to about 630 microns. A thickness of the protective jacket 114 may range from about 250 microns to about 1,040 microns. As shown in FIG. 1, a proximal end of the laser fiber 111 can be in communication with the laser source unit 180. The laser fiber 111 is configured to transmit laser light from a distal end to the proximal end.

With continued reference to FIG. 2A, in the illustrated embodiment, the temperature probe 110 includes a light diffuser 115 in communication with distal ends of the laser fiber 111 and the optical fiber 120. The light diffuser 115 is configured to diffuse light emitted from the laser fiber 111 and the optical fiber 120 in a desired pattern, such as conical, 360 degrees side fire, 180 degrees side fire, 90 degrees side fire, and spherical. The light diffuser 115 can be of any suitable form to diffuse light. For example, the light diffuser 115 can be a cylindrical rod as depicted in FIG. 2A. In other embodiments, the light diffuser 115 can be a lens shaped to diffuse emitted light in a desired direction In some embodiments, the light diffuser 115 or a separate lens may be configured to direct light to the optical fiber 120. The light diffuser 115 or lens can be of any suitable form to receive light and can be shaped to receive light from a desired direction.

As illustrated in FIGS. 2A and 2B, in some embodiments, the catheter assembly 150 includes a tubular body 151 having a wall 156 defining an outer lumen 155 extending therethrough, an inner tube 153 defining an inner lumen 154, a tip 152 disposed at a distal end of the tubular body 151, and a connector 160 coupled to a proximal end of the tubular body 151, as shown in FIG. 1. The tubular body 151 may be formed from any suitable material that permits transmission of light through a wall 158 of the tubular body 151. For example, in some embodiments, the tubular body 151 can be formed of polycarbonate polycarbonate or any other optically transparent plastic material that can withstand environmental temperatures in excess of 100 degrees Celsius. Additionally, the tubular body 151 can be formed of glass, quartz, sapphire, and so forth. The tubular body 151 may have an outer diameter that ranges from about 1.0 mm to about 2.0 mm, and may be about 1.65 mm. The inner lumen 154 has a diameter sized to slidingly receive the temperature probe 110.

In the illustrated embodiment of FIGS. 2A and 2B, the tubular body 151 includes a plurality of nanodiamonds 157. The nanodiamonds 157 are shown embedded within and dispersed throughout a distal portion of the wall 156. In some embodiments, the nanodiamonds 157 may be dispersed circumferentially around the tubular body 151. In another embodiment, the nanodiamonds 157 can be dispersed in a longitudinal strip having an arc length ranging from about 15 degrees to about 180 degrees of a circumference of the tubular body 151. A length of the strip of nanodiamonds 157 may range from about 0.1 mm to about 150 mm. In other embodiments, the nanodiamonds 157 may be dispersed over a surface of the tubular body 151 as a coating such that the nanodiamonds 157 may directly contact adjacent tissue. Said another way, the nanodiamonds 157 can be disposed over the exterior surface of the tubular body 151 such that an outer surface of the nanodiamonds 157 directly contacts the adjacent tissue. When in direct contact with the adjacent tissue, the nanodiamonds 157 can thermally transition to a temperature of the adjacent tissue.

In certain embodiments, each of the plurality of nanodiamonds 157 can have a diameter of less than 100 nm and ranging from about 2 nm to about 8 nm and may be spherical or elliptical in shape. The nanodiamonds 157 can include a core having a defect, such as a nitrogen-vacancy color center. The nitrogen-vacancy color center may be configured to be excited by light having a wavelength of about 532 nm. When excited, the nitrogen-vacancy color center may fluoresce, emitting a fluorescent light having a wavelength range of about 600 nm to about 800 nm. An intensity of the emitted fluorescent light may be correlated with a temperature of the nanodiamonds 157. In other words, the intensity of the emitted fluorescent light from the excited nitrogen-vacancy color center can increase or decrease as the temperature of the nanodiamonds 157 changes as influenced by a temperature of a surrounding environment, such as tissue. The nitrogen-vacancy color center can be resistant to inferences such as electrostatic, magnetic, light, etc., such that the fluorescent light emitted by the nitrogen-vacancy color center is substantially free of interference.

As depicted in FIG. 2A, the tip 152 may include a conical shape configured to pass through soft tissue without cutting or otherwise damaging the soft tissue. In other embodiments, the tip 152 includes any suitable shape that can pass through soft tissue without cutting or otherwise damaging the soft tissue. For example, the tip 152 may include a bullet nose shape, a beveled shape, or other suitable shape.

As shown in FIG. 2A, in some embodiments the tip 152 is integral with the tubular body 151 and can be formed from the same material as the tubular body 151. The tip 152 can be formed by heat forming in a dye. In other embodiments, the tip 152 can be a separate component and is fixedly coupled to a distal end of the tubular body 151 using any suitable technique, such as welding, gluing, bonding, etc. In this embodiment, the tip 152 can be formed from a material different than the tubular body 151. For example, the tip 152 of this embodiment may be formed from a material that is stiffer or softer than the material of the tubular body 151 to improve insertability (e.g., trackability and/or pushability) of the tubular body 151.

In the depicted embodiment of FIG. 1, the connector 160 is coupled to a proximal end of the tubular body 151 and to a distal end of the sleeve 140. The connector 160 may be configured to secure the temperature probe 110 in a longitudinal position relative to the catheter assembly 150 and to provide a seal around the temperature probe 110. In some embodiments, the connector 160 may include a manifold 161 in fluid communication with the inner lumen 154 and the outer lumen 155 such that fluid can be circulated within the tubular body 151 to cool a distal portion of the temperature probe 110. For example, the manifold 161 can include an inflow tube 162 in fluid communication with the outer lumen 155 and an outflow tube 163 in fluid communication with the inner lumen 154. When in use, fluid (e.g., saline) may flow into the manifold 161 from the inflow tube 162, through the outer lumen 155 to a distal end of the tubular body 151, return to the manifold 161 through the inner lumen 154, and exit the manifold 161 into the outflow tube 163. As the saline flows through the inner lumen 154, the saline may surround the temperature probe 110 to cool it during a laser ablation procedure.

The temperature monitoring unit 170, as shown in FIG. 1, may be communication with the proximal end of the optical fiber 120 and configured to receive light that is transmitted through the optical fiber 120. The optical fiber 120 may be configured to interface with the nanodiamonds 157. For example, the light transmitted by the optical fiber 120 may illuminate the nanodiamonds 157 and the optical fiber 120 may also receive the light of the illuminated nanodiamonds 157. The temperature monitoring unit 170 may include the temperature sensor 172 configured to receive the nanodiamond fluorescent light from the optical fiber 120 and analyze an intensity of the nanodiamond fluorescent light to calculate a temperature of the tissue adjacent the nanodiamonds 157.

In some embodiments, the temperature probe 110 may not use the optical fiber 120 to transmit light, instead the temperature probe 110 may rely on the laser light from the laser ablation procedure to illuminate the nanodiamonds 157. For example, the laser light transmitted through the laser fiber 111 may activate the nitrogen-vacancy color centers of the nanodiamonds 157 causing the nitrogen-vacancy color centers to fluoresce. The nanodiamond fluorescent light may then be transmitted to the temperature sensor 172 through the optical fiber 120 to analyze the intensity of the nanodiamond fluorescent light to calculate a temperature of the tissue adjacent the nanodiamonds 157.

In some embodiments, the temperature sensor 172 may be integrated directly on the temperature probe 110. For example, the temperature sensor 172 may be on a distal portion of the temperature probe 110 and interface with the nano diamond strip directly. In some embodiments As illustrated in FIG. 1, the light source 173 is in communication with the optical fiber 120. The light source 173 can be configured to emit light capable of exciting the nitrogen-vacancy color centers of the nanodiamonds 157. The irradiated light may have a wavelength ranging from about 380 nm to about 1500 nm, including about 532 nm.

Figure 3A:
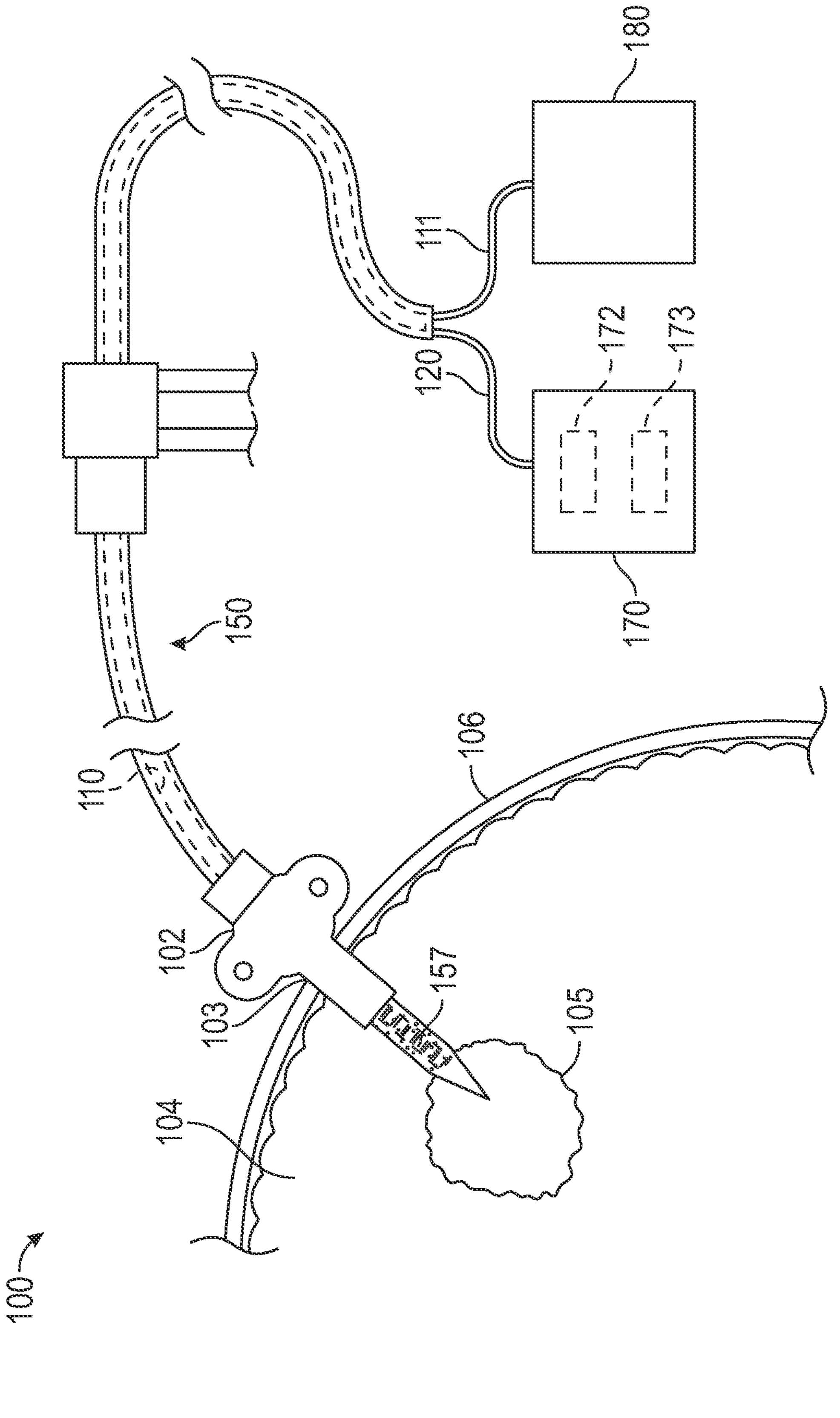
FIG. 3A is a schematic view of the laser ablation system of FIG. 1 with the nanodiamond thermometer positioned in a tissue prior to a laser ablation procedure.

In certain embodiments, the temperature monitoring system 100 can be used to measure a baseline temperature of a tissue prior to an MRI-guided laser ablation procedure. In another embodiment, the temperature monitoring system 100 can be used to measure an intra-procedure temperature of a tissue during an MRI-guided procedure. For example, in one embodiment, as depicted in FIG. 3A, a bone anchor 102 can be inserted through a first bore hole 103 disposed through a skull 106 of a patient. The catheter assembly 150 can be inserted through the bone anchor 102 into the brain tissue 104 such that the nanodiamonds 157 are disposed adjacent the brain tissue 104. The temperature probe 110 may be inserted into the catheter assembly 150. The light source 173 of the temperature monitoring unit 170 may be activated to emit a light through the optical fiber 120 to its distal end. The emitted light can excite the nitrogen-vacancy color centers of the nanodiamonds 157 such that the nitrogen-vacancy color centers emit a fluorescent light. The fluorescent light may be transmitted from the distal end of the optical fiber 120 to the temperature sensor 172 of the temperature monitoring unit 170. The temperature sensor 172 can process the intensity of the received fluorescent light to calculate the baseline temperature of the brain tissue 104 adjacent the nanodiamonds 157 prior to the MRI-guided laser ablation procedure. In some embodiments, the catheter assembly 150 may be inserted through a second bore hole disposed adjacent the first bore hole 103.

Figure 3B:
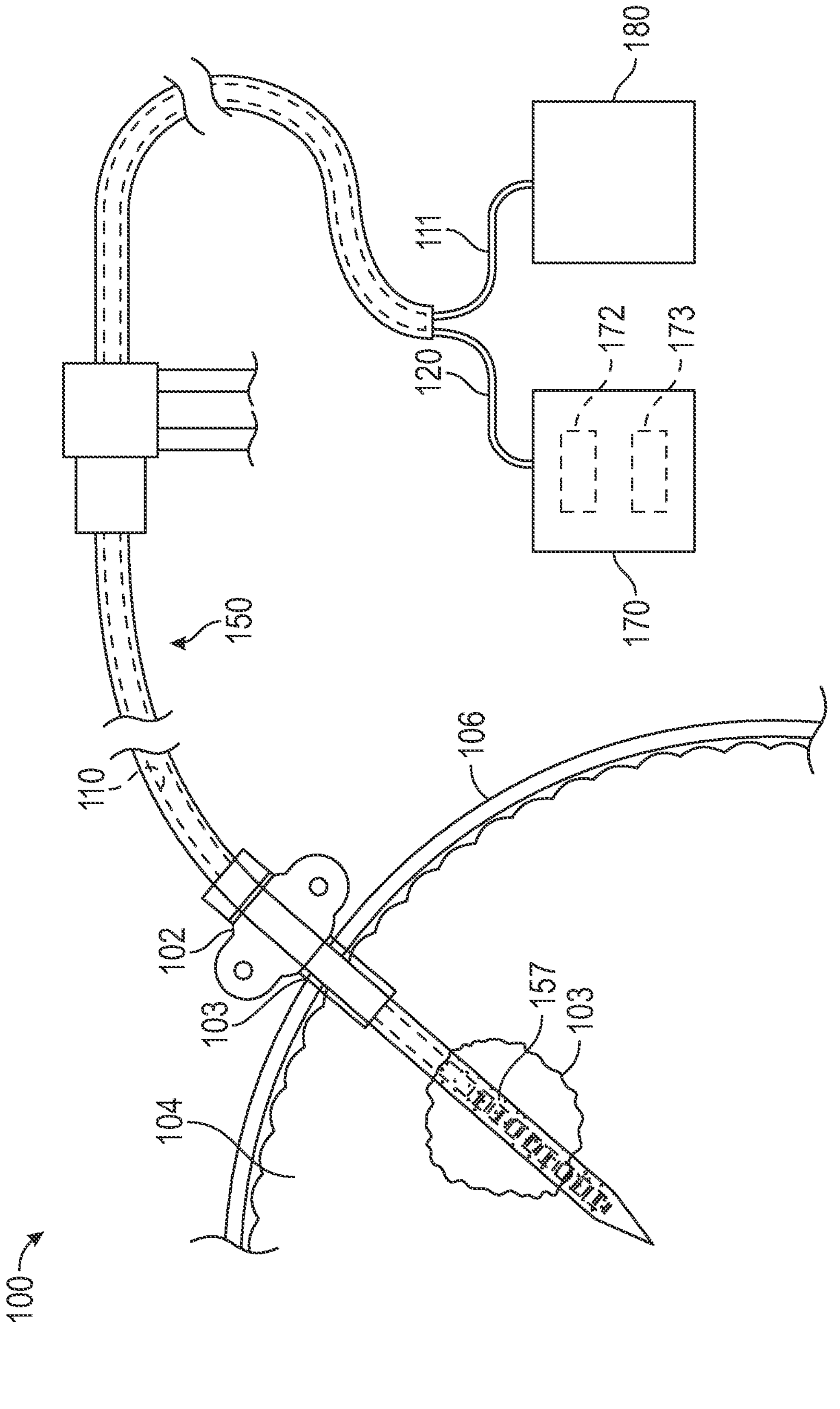
FIG. 3B is a schematic view of the laser ablation system of FIG. 1 with the nanodiamond thermometer positioned in a tumor during a laser ablation procedure.

In another embodiment, as depicted in FIG. 3B, the bone anchor 102 can be inserted through the first bore hole 103 disposed through the skull 106 of the patient. The catheter assembly 150 can be inserted through the bone anchor 102 into the brain tissue 104 such that the nanodiamonds 157 are disposed within tumor tissue 105. The temperature probe 110 may be inserted into the catheter assembly 150. The light source 173 of the temperature monitoring unit 170 may be activated to emit a light through the optical fiber 120 to its distal end. The emitted light can excite the nitrogen-vacancy color centers of the nanodiamonds 157 such that the nitrogen-vacant color centers emit a fluorescent light. The fluorescent light may be transmitted from the distal end of the optical fiber 120 to the temperature sensor 172 of the temperature monitoring unit 170. The temperature sensor 172 can process the intensity of the received fluorescent light to calculate the baseline temperature of the tumor tissue 105 adjacent the nanodiamonds 157 prior to and/or during the MRI-guided laser ablation procedure.

Figure 4A:
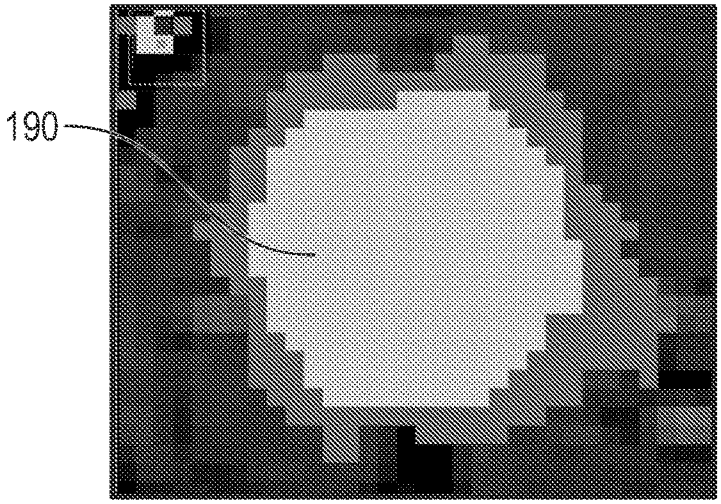
FIG. 4A is an illustration of a thermal damage estimate using a default baseline temperature of 37 degrees C.
Figure 4B:
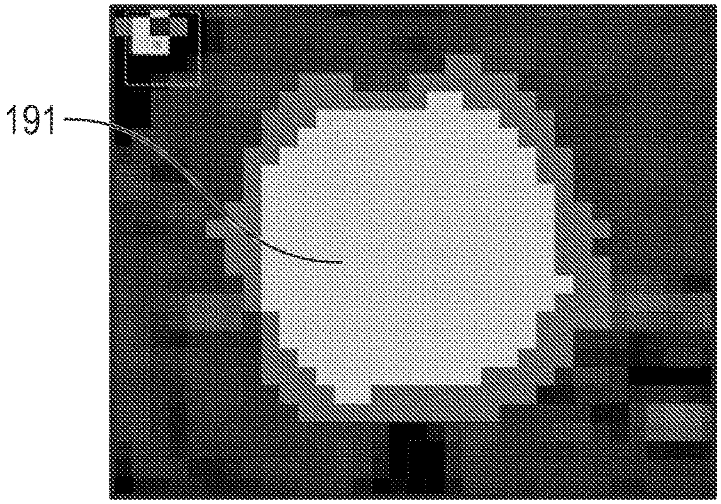
FIG. 4B is an illustration of a thermal damage estimate using a measured baseline temperature of 35 degrees C.
Figure 4C:
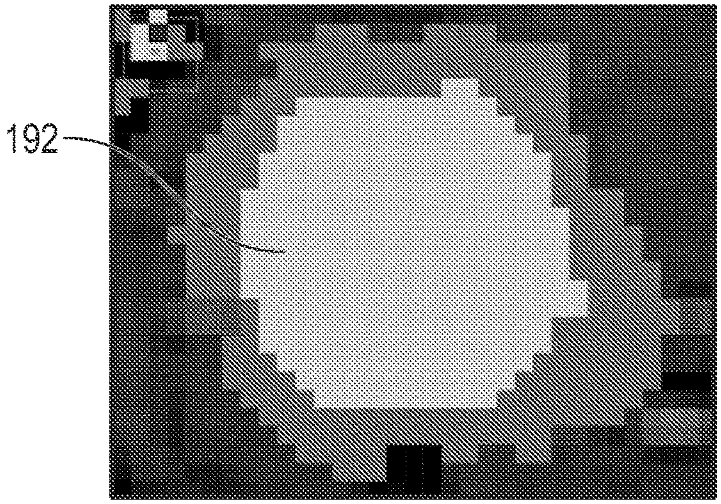
FIG. 4C is an illustration of a thermal damage estimate using a measured baseline temperature of 39 degrees C.

In some embodiments, the baseline temperature measured by the temperature monitoring system 100 can be an input of a laser ablation control system to provide a TDE of a laser ablation by the laser ablation control system. By providing a baseline temperature the laser ablation control system can calculate a more precise TDE in comparison of using a default baseline temperature. For example, as illustrated in FIG. 4A, a TDE 190 using a default baseline temperature of 37 degrees C. is overestimated in comparison to a TDE 191 of FIG. 4B using a measured baseline temperature of 35 degrees C. The overestimation may result in non-ablation of the tumor tissue 105. FIG. 4A also depicts the TDE 190 using the default temperature of 37 degrees C. is an under-estimation in comparison to a TDE 192 of FIG. 4C using a measured baseline temperature of 39 degrees C. The under-estimation may result in ablation of brain tissue 104 beyond a margin of the tumor tissue 105.

In some embodiments, the TDE can be used to establish settings for a variety of parameters of the laser ablation control system. For example, the settings may include ablation time, laser frequency, laser amplitude, tumor temperature, ablation boundary, etc.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A temperature monitoring system, comprising:

a probe comprising an optical fiber cable configured to emit light and receive light;

a sensor coupled to the probe to process the received light; and a catheter comprising a plurality of nanodiamonds embedded in a wall of the catheter, wherein the probe is configured to be selectively slidingly disposed within the catheter and the optical fiber cable is configured to interface with the nanodiamonds; and wherein the sensor determines a tissue temperature based on the received light that is emitted from the nanodiamonds.

2. The temperature monitoring system of claim 1, wherein the optical fiber cable comprises a light emitting fiber and a light receiving fiber.

3. The temperature monitoring system of claim 1, wherein the probe further comprises a laser fiber for laser ablation.

4. The temperature monitoring system of claim 1, wherein each nanodiamond of the plurality of nanodiamonds comprises a nitrogen-vacancy color center, and wherein the optical fiber cable is configured to emit light to excite each of the nitrogen-vacancy color centers, and wherein the optical fiber cable is configured to receive fluorescent light from the excited nitrogen-vacancy color centers.

5. The temperature monitoring system of claim 4, wherein the emitted light comprises a wavelength of 532 nm.

6. The temperature monitoring systems of claim 4, wherein the fluorescent light comprises a wavelength ranging between 600 nm and 800 nm.

7. The temperature monitoring system of claim 4, wherein an intensity of the fluorescent light changes in correlation with a temperature change of each nanodiamond of the plurality of nanodiamonds.

8. The temperature monitoring system of claim 1, wherein the plurality of nanodiamonds are embedded in a longitudinal strip along at least a portion of a length of the catheter.

9. The temperature monitoring system of claim 8, wherein a width of the longitudinal strip comprises an arc length of from 15 degrees to 180 degrees of a circumference of the catheter.

10. The temperature monitoring system of claim 1, wherein the probe is configured to measure a baseline tissue temperature prior to initiation of a laser ablation procedure.

11. The temperature monitoring system of claim 10, wherein the baseline tissue temperature is provided to a laser ablation system to determine settings of the laser ablation procedure.

12. The temperature monitoring system of claim 1, wherein the probe is configured to measure an intra-ablation tissue temperature during a laser ablation procedure.

13. The temperature monitoring system of claim 12, wherein the intra-ablation tissue temperature is provided to a laser ablation system to adjust settings of the laser ablation procedure intra-procedurally.

14. The temperature monitoring system of claim 1, wherein in the nanodiamonds are configured to interface directly with a patient's tissue to measure the tissue temperature.

15. The temperature monitoring system of claim 1, wherein the nanodiamonds are configured to thermally transition to the tissue temperature.

16. A method of measuring a baseline tissue temperature prior to a laser ablation procedure, comprising:

positioning a temperature probe adjacent to or within a target tissue structure, wherein the temperature probe is configured to be selectively slidingly disposed within a catheter comprising a nanodiamond embedded in a wall of the catheter;

measuring the baseline tissue temperature adjacent or within the target tissue structure prior to initiation of the laser ablation procedure;

performing laser ablation of the target tissue structure based on the baseline tissue temperature; and determining a thermal damage estimate of the target tissue structure.

17. The method of claim 16, further comprising:

exciting a nitrogen-vacancy color center of the nanodiamond with light emitted from an optical fiber from within the catheter; and receiving fluorescent light from the excited nitrogen-vacancy color center with the optical fiber.

18. The method of claim 17, further comprising:

receiving data from the optical fiber by a processing unit; and performing a spectral analysis of the data to determine the baseline tissue temperature.

19. The method of claim 18, further comprising providing the measured baseline tissue temperature to a laser ablation system to determine laser ablation procedure settings.

20. The method of claim 19, wherein the laser ablation procedure settings include any one of ablation time, laser frequency, laser amplitude, tumor temperature, ablation boundary, or any combination thereof.

21. The method of claim 17, further comprising:

positioning the nanodiamond and the optical fiber at a position within a target tissue structure; and maintaining the position of the nanodiamond and the optical fiber within the target tissue structure during the laser ablation procedure.

22. The method of claim 21, wherein the target tissue structure is a tumor.

23. The method of claim 17, further comprising:

positioning the nanodiamond and the optical fiber at a position adjacent a target tissue structure; and removing the nanodiamond and the optical fiber prior to the laser ablation procedure.

24. The method of claim 23, wherein the target tissue structure is a tumor.

25. The method of claim 17, further comprising imaging the target tissue structure during the laser ablation procedure using an MRI system, wherein the temperature probe captures a temperature of the tissue while the MRI system is in use.

26. A method of measuring an intra-procedure tissue temperature during a laser ablation procedure, comprising:

positioning a temperature probe within a target tissue structure, wherein the temperature probe is configured to be selectively slidingly disposed within a catheter comprising a nanodiamond embedded in a wall of the catheter;

performing laser ablation of the target tissue structure;

measuring the intra-procedure tissue temperature of the target tissue structure during laser ablation of the target tissue structure; and determining a thermal damage estimate based on the measured intra-procedure tissue temperature of the target tissue structure.

27. The method of claim 26, further comprising:

exciting a nitrogen-vacancy color center of the nanodiamond with light emitted from an optical fiber from within the catheter; and receiving fluorescent light from the excited nitrogen-vacancy color center with the optical fiber.

28. The method of claim 27, further comprising performing a spectral analysis of the received fluorescent light to determine the tissue temperature.

29. The method of claim 28, further comprising providing the measured intra-procedure temperature to a laser ablation system during the laser ablation procedure to determine laser ablation procedure settings.

30. The method of claim 29, wherein the laser ablation procedure settings include any one of ablation time, laser frequency, laser amplitude, tumor temperature, ablation boundary, or any combination thereof.

31. The method of claim 27, further comprising:

positioning the nanodiamond and the optical fiber at a position within a target tissue structure; and maintaining the position of the nanodiamond and the optical fiber within the target tissue structure during the laser ablation procedure.

32. The method of claim 31, wherein capture the intra-procedure tissue temperature of the tissue is measured while an image of the tissue is captured with an MRI system.

33. The method of claim 27, further comprising imaging the target tissue structure during the laser ablation procedure using an MRI system.

34. A laser ablation system, comprising:

an ablation probe, comprising:

a laser fiber configured to emit laser energy to ablate tissue;

one or more optical fibers configured to emit and/or receive light; and a catheter comprising a plurality of nanodiamonds embedded in a wall of the catheter, wherein the ablation probe is configured to be selectively slidingly disposed within the catheter; and wherein the nanodiamonds are configured to thermally couple with adjacent tissue and to indicate a measure of tissue temperature in response to light emitted from the one or more optical fibers.

35. The laser ablation system of claim 34, wherein each nanodiamond of the plurality of nanodiamonds comprises a nitrogen-vacancy color center, and wherein the one or more optical fibers are configured to emit light to excite each of the nitrogen-vacancy color centers, and wherein the one or more optical fibers are configured to receive fluorescent light from the excited nitrogen-vacancy color centers.

36. The laser ablation system of claim 35, wherein the emitted light comprises a wavelength of 532 nm.

37. The laser ablation system of claim 35, wherein the fluorescent light comprises a wavelength ranging between 600 nm and 800 nm.

38. The laser ablation system of claim 35, wherein an intensity of the fluorescent light changes in correlation with a temperature change of each nanodiamond of the plurality of nanodiamonds.

39. The laser ablation system of claim 35, wherein a baseline tissue temperature is measured prior to initiation of a laser ablation procedure.

40. The laser ablation system of claim 39, wherein the baseline tissue temperature is provided to a laser ablation system to determine settings of the laser ablation procedure.

41. The laser ablation system of claim 34, wherein the plurality of nanodiamonds are embedded in a longitudinal strip.

42. The laser ablation system of claim 41, wherein a width of the longitudinal strip comprises an arc length of from 15 degrees to 180 degrees of a circumference of the catheter.

43. The laser ablation system of claim 34, wherein an intra-ablation tissue temperature is measured during a laser ablation procedure.

44. The laser ablation system of claim 43, wherein the intra-ablation tissue temperature is provided to a laser ablation system to adjust parameters of the laser ablation procedure intra-procedurally.

45. The laser ablation system of claim 34, further comprising:

a processing unit to:

measure, via the light received by the one or more optical fibers, a tissue temperature adjacent the nanodiamonds.

46. The laser ablation system of claim 45, wherein the tissue temperature is measured while an image of the tissue is captured with an MRI system.

47. A thermometer, comprising:

a probe comprising an optical fiber; and a catheter comprising a plurality of nanodiamonds embedded in a wall of the catheter configured to thermally engage tissue of a patient, wherein the optical fiber is used to optically interact with the plurality of nanodiamonds and thereby capture a temperature of the tissue while an image of the tissue is captured with an MRI system.

48. The thermometer of claim 47, wherein in the plurality of nanodiamonds are configured to interface directly with a patient's tissue to capture the temperature of the tissue.

49. The thermometer of claim 47, wherein the plurality of nanodiamonds are configured to thermally transition to the temperature of the tissue.

50. The thermometer of claim 47, wherein the temperature of the tissue is captured prior to a laser ablation procedure.

51. The thermometer of claim 47, wherein the temperature of the tissue is captured during a laser ablation procedure.

* * * * *